Figure 1:
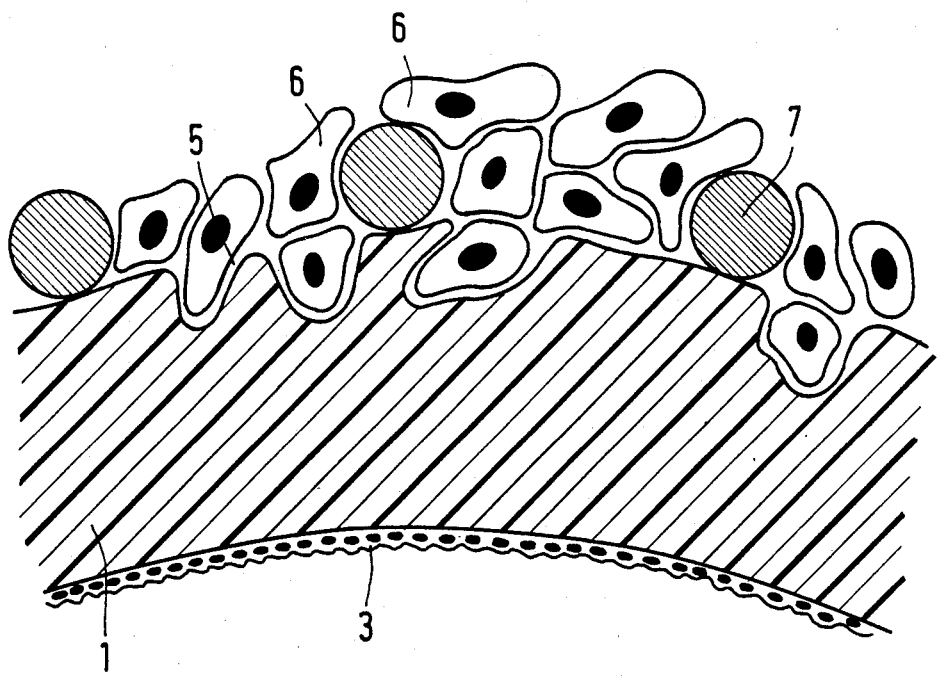

United States Patent [19]

Turina et al.

[11] Patent Number: 4,804,382

[45] Date of Patent: Feb. 14, 1989

[54] ARTIFICIAL VESSEL

[75] Inventors: Marko Turina, Zurich; Peter Bittmann, Herrliberg, both of Switzerland

[73] Assignee: Sulzer Brothers Limited, Winterthur, Switzerland

[21] Appl. No.: 51,659

[22] Filed: May 19, 1987

[30] Foreign Application Priority Data

Jun. 2, 1986 [CH] Switzerland .................... 2220/86

[51] Int. Cl.$^4$ ............................................. A61F 2/06
[52] U.S. Cl. .......................................... 623/1; 623/11; 623/66; 435/240.2
[58] Field of Search .................... 427/2; 428/304.4; 435/174, 180, 182, 240; 623/1, 11, 12, 66

[56] References Cited

U.S. PATENT DOCUMENTS 4,355,426 10/1982 MacGregor ........................... 623/1
4,546,500 10/1985 Bell ......................................... 623/1

FOREIGN PATENT DOCUMENTS 3422639 12/1985 Fed. Rep. of Germany ........ 623/66

Primary Examiner—Richard J. Apley
Assistant Examiner—Paul Prebilic
Attorney, Agent, or Firm—Kenyon & Kenyon

[57] ABSTRACT

The artificial vessel has a membrane of at least semi-permeable bio-inert synthetic material with a mono-layer of endothelial cells on the internal surface and a layer of smooth elastic fiber-generating muscle cells on the outer surface. The membrane may be made pore-less or may be made with a network of opened micro-pores filled with an aqueous gel to provide a smooth internal surface on which the endothelial cells may be coated.

11 Claims, 1 Drawing Sheet

ARTIFICIAL VESSEL

This invention relates to an artificial vessel. More particularly, this invention relates to an artificial vessel wall for arterial vessels having an inner diameter of less than seven millimeters.

Heretofore, various types of arterial substitutes have been known for vessels, such as blood vessels. Further, experience has taught that substances which are impermeable to fluids and especially to water, nutrients, tissue fluid and metabolic products are not suitable as artificial vessel walls. This is because the movements of the tissue fluids through the vessel walls are largely hindered. This, in turn, leads to disturbances in the physiological equilibrium as well as to severe body reactions. Thus, the artificial vessel walls must have at least some permeability of fluids.

The problem of providing arterial substitutes for large vessels, for example, in the area between the aorta and the groin area has been largely solved through the use of textile prostheses and the use of expanded polytetrafluoroethylene prostheses. In these relatively large vessels, the permeability of the vessel wall is achieved through the use of a textile structure or through a stretch-distend process with tissue growing in simultaneously from the outside to provide a simultaneous fixation in the body.

However, in the case of small artificial vessels, for example, of the kind having a small lumen with an inner diameter below seven millimeters, there is a tendency to occlusion. In this respect, the interaction between blood and synthetic material leads to the formation of a fibrin layer with a consequent narrowing of the lumen. This, in turn, causes the velocity of the blood flow to decrease and further favors depositions and thrombosis developments of the prosthesis. In order to address this difficulty, it has been known from German Pat. No. 3422639 to provide glandula prostheses in which the inside of the vessel is lined before implantation with a gap-less monolayer of the patient's own endothelial cells.

It is also known that fluid-permeable gel substances, for example, aqueous gels of an agar-agar or polyacrylamide base have sufficient permeability. However, such gel substances are unsuitable for use as a vessel wall since the substances do not have sufficient mechanical strength, for example, to withstand the pressure pulsations of an arterial blood stream.

Permeable artificial vessels which fulfill the described demands have used elastic membranes of bio-inert synthetic materials, such as, a poreless polymer of poly-amino acids and urethane. In addition, membranes of a thickness of from 0.2 to 1 millimeters which consist of a synthetic material, such as polyurethane, in which the permeability is ensured through completely opened pores have also proven suitable. In this latter case, since a simultaneous fixation is also desired through a ingrowth of a tissue from the outside or a growing on of tissue on the outside, the pore sizes must be in a range of from 10 to 50 $\mu$m and, preferably, 30 $\mu$m. If necessary, it is also possible to increase the mechanical strength of the membrane by "armouring", for example, with bio-inert fiber material.

In order for a monolayer of endothelial cells to adhere and to survive, the cells must form a closed continuous coating or lining on the vessel. Also, the adhesion of the cells on synthetic material, on which they grow to form a basal membrane of type IV collagen, has to be so great that they are not torn away by the blood stream.

Accordingly, it is an object of the invention to improve the regeneration, adhesion and viability of a monolayered lining of endothelial cells on a mechanically stable elastic vessel wall of a vessel having a small lumen.

It is another object of the invention to provide an artificial vessel having a relatively small lumen.

Briefly, the invention provides an artificial vessel which is comprised of a tubular membrane of at least semi-permeable bio-inert synthetic material having a monolayer of endothelial cells on an internal surface for contact with a blood stream and a layer of smooth elastic fiber-generating muscle cells on an outer surface. The layer of fiber-generating cells may be applied as a single layer or as a multi-layer. Further, the fiber-generating muscle cells can be applied simultaneously with the endothelial cells or in separate steps.

The provision of the live muscle cells and the endothelial cells on the surfaces of the vessel permit biochemical and physiological interactions to occur which lead to an improvement of the ability of the live cells to survive on the synthetic membrane. Moreover, the elastic fibers formed by the muscle cells reinforce the membrane as a vessel wall and ensure the elasticity of the vessel wall even if the synthetic material of the membrane suffers potential changes over a long term.

If the vessel wall is made of a synthetic material with micropores in a range of from 10 to 50 $\mu$m the vessel may be provided with a means for smoothing the inner surface of the membrane while at least partially maintaining permeability of the membrane. In this respect, it has been shown that endothelial cells cannot grow over the large pores of a porous membrane so that a closed layer of endothelial cells, if at all, can only be cultured with difficulty. By "smoothing" the internal surface of the membrane, for example by filling or covering of the "large" pores, the endothelial cells can be readily grown over these otherwise disruptive sites on the internal surface so as to form a closed, continuous and firmly adhering mono-layer.

In one embodiment, a microporous membrane can be prepared, for example, in accordance with the known process of phase separation at low temperatures. For smoothing the surface of the internal wall of such a membrane, two possibilities exist and both can be used to good advantage. In one case, the micropores can be filled with an aqueous gel which is permeable to molecules of a molecular weight up to 100,000 Dalton. Aqueous gels which are suitable for this purpose include agar-agar and poly-acrylamide gels. In a second case, the surfaces of the micropores on the bloodstream side of the membrane can be closed by means of a porous layer in which the diameter of the pores of the layer are approximately the same size as the dimensions of the endothelial cells. In this case, the porous layers can be made in the form of membranes which are known from ultrafiltration techniques.

As is well known, natural vessel walls are formed in such a way that with increasing internal pressure, they show an elastic dilation which moves toward an upper limit as the pressure increases. Membranes of synthetic material possess these properties only to an imperfect degree. For that reason, it is expedient to limit the dilation of the membrane by means of a support structure. For example, the support structure may consist of a textile knitwear having a stitch width between 0.2 to 2 millimeters. In particular, the support structure may be made of a braided construction consisting of individual spirally arranged monofilaments of polyester threads with a diameter of 10 to 40 μm. The braiding, the individual filaments of which are practically inelastic, achieves a certain elasticity through the textile structure in that the individual filaments arrange themselves around each other in response to pressure changes. Experimental tests have shown that the linear extensibility of an artificial wall can be 0.03 to 0.1 percent per millimeter Hg pressure increase in a pressure range of from 80 to 150 millimeters Hg. The spiral structure of the braided materials provides a high resistance against buckling and thus lends to the membrane an increased kinking stability.

Figure 2:
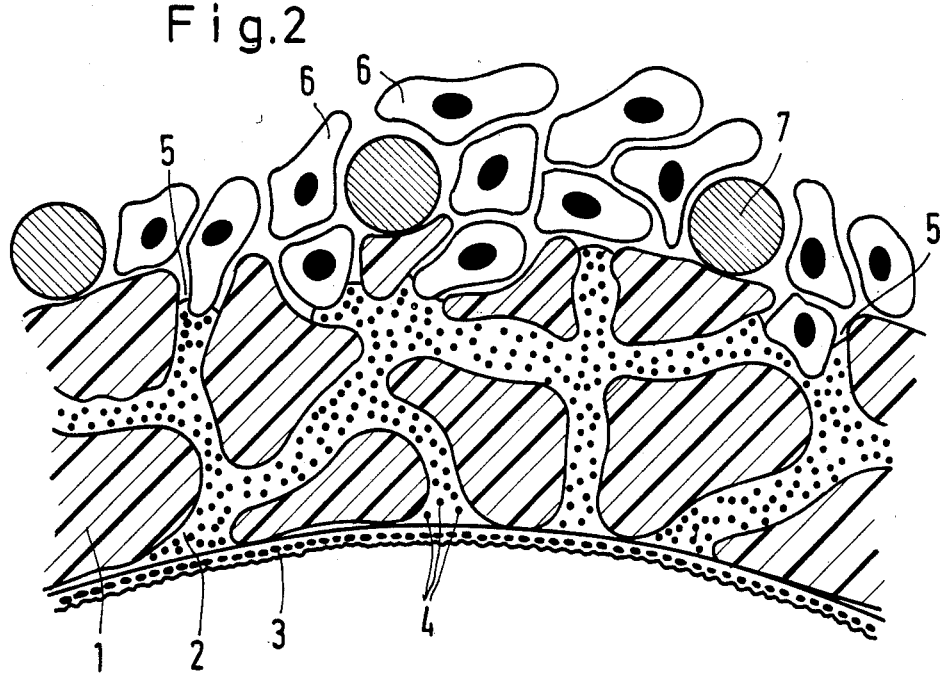

These and other objects and advantages of the invention will become more apparent from the following detailed description taken in conjunction with the accompanying drawings wherein:

FIG. 1 illustrates an enlarged schematic cross sectional view through a wall of an artificial vessel constructed in accordance with the invention; and FIG. 2 illustrates a view similar to FIG. 1 of a modified artificial vessel in accordance with the invention.

Referring to FIG. 1, the artificial vessel includes a tubular membrane of semi-permeable bio-inert synthetic material which is of a thickness of, for example, between 0.2 and 1 millimeters. In addition, a monolayer of live endothelial cells 3 is disposed on the internal surface of the membrane 1 for contact with a blood stream.

In addition, the outer surface of the membrane 1 is provided with hollow spaces 5 into which live cells 6 may grow for fixation of the artificial vessel in the body. The cells 6 are formed of smooth elastic fiber-generating muscle cells (SMC: smooth muscle cells) which are cultured in a known procedure and applied to the membrane 1 in a mono- or multi-layer.

These smooth muscle cells 6 serve through their physiological and biochemical interaction through the membrane 1 to enhance the "compatibility" of the artificial vessel in the body and, thus, the ability to survive and the vitality of the endothelial cells 3. In addition, the muscle cells 6 serve to increase the mechanical stability of the artificial vessel due to the elasticity of the cells 6. The physiological and biochemical interactions between the endothelial cells 3 and muscle cells 6 are made possible not only by the permeability of the membrane 1 but also of the elasticity of the synthetic material of the membrane 1 which permits the pressure pulse curves of the blood stream to be transmitted to the muscle cells 6 in order to stimulate production of elastic fibers (elastin).

Since the dilation of natural vessels and that of enthothelial cells is limited, a support structure is provided about the membrane 1 in order to limit dilation of the membrane to that of a naturally occurring vessel. In this respect, the support structure is formed of individual threads 7 with a low degree of elasticity, for example, inelastic monofilaments of polyester with a diameter of 10 to 40 μm. As indicated, the threads 7 are distributed over the outer surface of the membrane. For a peripherally closed synthetic vessel resembling an artery, the threads 7 are applied in the form of a braided material, the monofilaments of which extend spirally and which has a limited elasticity due to the mechanical shift of the individual threads 7. The braided material may have stitch widths in the range of from 0.2 to 2 millimeters.

Together with the thicknesses of the thread 7, the stitch widths permit a limited linear elasticity of 0.03 to 0.1 percent per millimeter Hg pressure increase in a physiological range of internal pressure of between 80 to 150 millimeters.

As indicated in FIG. 1, the semi-permeable membrane 1 may be made of a poreless polymer, for example of polyamino acids and urethane.

Referring to FIG. 2, the membrane 1 may be made of a synthetic material with completely open micropores, for example of a diameter at least partially between 10 and 50 μm and preferrably 30 μm. The synthetic material may be a polyurethane and may be produced according to a phase separation process at low temperatures. As indicated, the network of micropores 2 are opened at the outer surface as well as the inner surface of the membrane 1.

Since endothelial cells, in general, cannot or can only with great difficulty grow over hollow spaces having a diameter which is a multiple of their own dimensions, a means is provided to smooth the inner surface of the membrane 1. For example, this smoothing means may be in the form of an aqueous gel 4 which fills the micropores 2 without affecting the permeability membrane 1 to an undue degree. The gel 4 may be a 6% agarose or a 12 to 18% polyacrylamide gel which can be filled into the micropores using a known immersion process. After immersion, the gel is partially removed from the outer surface of the membrane 1 in order to create the hollow spaces 5 for the ingrowth of the cells 6.

The preparation of the "fill" gel may take place using different known procedures combined with each other. Within the framework of these known procedures, the agarose gel may be conditioned, for example, through electrical surface charges to improve the adhesion of live cells.

Sterilization of the vessel to be implanted or the individual parts of the vessel may take place by chemical means through immersion in sterilizing solutions.

Of note, the thickness of the synthetic membrane 1 should be as small as possible in order to permit the desired interactions between the endothelial cells and the muscle cells 6 and as large as possible for ease of handling by the surgeon.

The invention thus provides an artificial vessel in which the growth, adhesion and viability of endothelial cells on the internal surface is improved.

Further, the invention provides an artificial vessel which has long term body compatibility.

Still further, the invention provides an artificial vessel having an elasticity which can be maintained over a relatively long term.

What is claimed is:

1. An artificial vessel comprising
   a tubular membrane of at least semi-permeable bio-inert synthetic material;
   a monolayer of endothelial cells on an internal surface of said membrane for contact with a blood stream; and
   a layer of smooth elastic fiber-generating muscle cells on an outer surface of said membrane.

2. An artificial vessel as set forth in claim 1 wherein said membrane is a poreless polymer of polyamino acids and urethane.

3. An artificial vessel as set forth in claim 1 wherein said membrane is a synthetic material with completely open micropores of a diameter between 10 and 50 μm.

4. An artificial vessel as set forth in claim 3 wherein said pores have a diameter of 30 μm.

5. An artificial vessel as set forth in claim 1 which further comprises a support structure surrounding said membrane to limit dilation of said membrane.

6. An artificial vessel as set forth in claim 5 wherein at an internal pressure of 80 to 150 mm Hg, said membrane has a linear elasticity of 0.03 to 0.1% per mm Hg pressure increase.

7. An artificial vessel as set forth in claim 5 wherein said support structure consists of a textile knitwear having a stitch width between 0.2 and 2 millimeters.

8. An artificial vessel as set forth in claim 7 wherein said support structure consists of braided material of individual spirally arranged filaments of polyester threads of a diameter of 10 to 40 μm.

9. An artificial vessael as set forth in claim 1 wherein said membrane has a thickness of from 0.1 to 1 millimeter.

10. An artificial vessel comprising
a membrane of at least semi-permeable bio-inert synthetic material and having a thickness of from 0.1 to 1 millimeter;
a monolayer of endothelial cells on an internal surface of said membrane for contact with a blood stream;
a layer of smooth elastic fiber-generating muscle cells on an outer surface of said membrane; and
a support structure surrounding said membrane to limit dilation of said membrane.

11. An artificial vessel as set forth in claim 10 wherein said support structure consists of braided material of individual spirally arranged filaments of polyester threads of a diameter of 10 to 40 μm.

* * * * *

UNITED STATES PATENT AND TRADEMARK OFFICE
CERTIFICATE OF CORRECTION

PATENT NO. : 4,804,382

DATED : Feb. 14, 1989

INVENTOR(S) : MARKO TURINA

It is certified that error appears in the above-identified patent and that said Letters Patent is hereby corrected as shown below:

Column 1, line 59 "of a tissue" should be -of tissue-

Column 2, line 53 "poly-acrylamide" should be -polyacrylamide-

Column 3, line  1 "0.2 to 2" should be -0.2 and 2-

Signed and Sealed this

Twenty-first Day of November, 1989

Attest:

JEFFREY M. SAMUELS

*Attesting Officer*   *Acting Commissioner of Patents and Trademarks*